US012253578B2

(12) United States Patent
Ogata et al.

(10) Patent No.: US 12,253,578 B2
(45) Date of Patent: Mar. 18, 2025

(54) SIGNAL VECTOR DERIVATION APPARATUS, METHOD, PROGRAM, AND RECORDING MEDIUM

(71) Applicant: ADVANTEST CORPORATION, Tokyo (JP)

(72) Inventors: Yuji Ogata, Miyagi (JP); Tomonori Yanagida, Miyagi (JP)

(73) Assignee: ADVANTEST CORPORATION, Tokyo (JP)

( * ) Notice: Subject to any disclaimer, the term of this patent is extended or adjusted under 35 U.S.C. 154(b) by 20 days.

(21) Appl. No.: 18/272,888

(22) PCT Filed: Mar. 7, 2022

(86) PCT No.: PCT/JP2022/009613
§ 371 (c)(1),
(2) Date: Jul. 18, 2023

(87) PCT Pub. No.: WO2022/230365
PCT Pub. Date: Nov. 3, 2022

(65) Prior Publication Data
US 2024/0094311 A1 Mar. 21, 2024

(30) Foreign Application Priority Data
Apr. 27, 2021 (JP) ................. 2021-074991

(51) Int. Cl.
*G01R 33/02* (2006.01)
(52) U.S. Cl.
CPC ............... *G01R 33/0206* (2013.01)
(58) Field of Classification Search
CPC G01R 33/0206; G01R 29/0814; G01R 33/00; H04B 17/204; H04B 17/0085; H01Q 1/243
See application file for complete search history.

(56) References Cited

U.S. PATENT DOCUMENTS 5,383,164 A * 1/1995 Sejnowski .......... G06F 18/2134
367/134
6,700,388 B1 * 3/2004 Mayor ............... G01R 29/0892
324/537

(Continued)

FOREIGN PATENT DOCUMENTS

CN 106970348 7/2017
JP 2002-028143 1/2002

(Continued)

OTHER PUBLICATIONS

International Search Report (ISR) from International Searching Authority (Japan Patent Office) in International Pat. Appl. No. PCT/JP2022/009613, dated May 10, 2022, together with an English language translation.

(Continued)

*Primary Examiner* — Jermele M Hollington
*Assistant Examiner* — Taqi R Nasir
(74) *Attorney, Agent, or Firm* — Greenblum & Bernstein, P.L.C.

(57) ABSTRACT

A signal vector derivation apparatus receives measurement results from a plurality of sensors that receive signals each represented by a vector having a predetermined direction and measure triaxial components orthogonal to each other and derives the direction of the vector. The measurement results from the sensors are each proportional to a sum of the triaxial components of the vector multiplied, respectively, by first coefficients. The signal vector derivation apparatus includes a spectrum deriving section and a direction deriving section. The spectrum deriving section derives a spectrum obtained based on the measurement results from the sensors and a sum of the first coefficients multiplied, respectively, by second coefficients, the spectrum having local maximum values within voxels in which signal sources that output the respective signals exist. The direction deriving section (Continued)

derives the direction of the vector based on the second coefficients used to obtain the spectrum.

15 Claims, 3 Drawing Sheets

(56) References Cited

U.S. PATENT DOCUMENTS

| | | | | |
|---|---|---|---|---|
| 6,957,172 | B2* | 10/2005 | Wegerich | G06F 18/00 |
| | | | | 702/70 |
| 2004/0046558 | A1* | 3/2004 | Matsumoto | G01V 3/081 |
| | | | | 324/67 |
| 2004/0077964 | A1 | 4/2004 | Nakai et al. | |
| 2006/0251303 | A1 | 11/2006 | He et al. | |
| 2009/0093964 | A1 | 4/2009 | Alberta et al. | |
| 2010/0049482 | A1 | 2/2010 | He et al. | |

FOREIGN PATENT DOCUMENTS

| | | |
|---|---|---|
| JP | 2003-038455 | 2/2003 |
| JP | 2007-020594 | 2/2007 |
| JP | 2009-172088 | 8/2009 |
| JP | 2009-534103 | 9/2009 |

OTHER PUBLICATIONS

Ishii H. et al., "Algorithm for Magnetocardiography Analysis Based on Multi Channel SQUID and Thoracic MR Images" In: Aine C.J., Stroink G., Wood C.C., Okada Y., Swithenby S.J. (eds), Biomag 96. Springer, New York, NY., 2000, pp. 261-262.

H. Kudo et al., "Multiple Signal Source Localization from Spatio-Temporal Magnetocardiogram", Proceedings of 1994 IEEE Nuclear Science Symposium—NSS'94, pp. 1832-1836.

* cited by examiner

SIGNAL VECTOR DERIVATION APPARATUS, METHOD, PROGRAM, AND RECORDING MEDIUM

TECHNICAL FIELD

The present invention relates to measuring of a signal such as a magnetic field.

BACKGROUND ART

There have conventionally been known methods (e.g. subspace methods (such as MUSIC method, SF, WSF)) of estimating the position of a signal source based on a result of measurement of a magnetic field (see Patent Literature 1 and Non-Patent Literatures 1 and 2). There has also been known measuring a magnetic field about a living organism (see Patent Literatures 2, 3, and 4).

CITATION LIST

Patent Literature

Patent Literature 1: Japanese Patent Application Publication No. 2009-534103
Patent Literature 2: Japanese Patent Application Publication No. 2009-172088
Patent Literature 3: Japanese Patent Application Publication No. 2007-020594
Patent Literature 4: Japanese Patent Application Publication No. 2002-028143
Non Patent Literature 1: Ishii H., Niki N., Nakaya Y., Nishitani H., Kang Y. M. (2000) "Algorithm for Magnetocardiography Analysis Based on Multi Channel SQUID and Thoracic MR Images" In: Aine C. J., Stroink G., Wood C. C., Okada Y., Swithenby S. J. (eds) Biomag 96. Springer, New York, NY. pp. 261-262.
Non Patent Literature 2: H. Kudo; T. Maemura; T. Saito "Multiple Signal Source Localization from Spatio-Temporal Magnetocardiogram" Proceedings of 1994 IEEE Nuclear Science Symposium—NSS '94 pp. 1832-1836

SUMMARY OF THE INVENTION

Technical Problem

It is an object of the present invention to improve the accuracy of measurement of a signal such as a magnetic field.

Means for Solving the Problem

According to the present invention, a signal vector derivation apparatus for receiving measurement results from a plurality of sensors that receive signals each represented by a vector having a predetermined direction and measure triaxial components orthogonal to each other and for deriving the direction of the vector, the measurement results from the sensors each proportional to a sum of the triaxial components of the vector multiplied, respectively, by first coefficients, includes: a spectrum deriving section arranged to derive a spectrum obtained based on the measurement results from the sensors and a sum of the first coefficients multiplied, respectively, by second coefficients, the spectrum having local maximum values within voxels in which signal sources that output the respective signals exist; and a direction deriving section arranged to derive the direction of the vector based on the second coefficients used to obtain the spectrum.

The thus constructed signal vector derivation apparatus receives measurement results from a plurality of sensors that receive signals each represented by a vector having a predetermined direction and measure triaxial components orthogonal to each other and derives the direction of the vector. The measurement results from the sensors are each proportional to a sum of the triaxial components of the vector multiplied, respectively, by first coefficients. A spectrum deriving section derives a spectrum obtained based on the measurement results from the sensors and a sum of the first coefficients multiplied, respectively, by second coefficients, the spectrum having local maximum values within voxels in which signal sources that output the respective signals exist. A direction deriving section derives the direction of the vector based on the second coefficients used to obtain the spectrum.

According to the signal vector derivation apparatus of the present invention, the vector may be a magnetic dipole moment or an electric dipole moment.

According to the signal vector derivation apparatus of the present invention, the vector may be an electric dipole moment, and the component of the vector in the same direction as that of the component of each measurement result may be zero.

According to the signal vector derivation apparatus of the present invention, the first coefficients may be defined based on the positional relationships between the respective voxels and the respective sensors.

According to the signal vector derivation apparatus of the present invention, any one or two of the second coefficients may be zero.

According to the signal vector derivation apparatus of the present invention, the spectrum may be obtained according to the MUSIC method.

According to the signal vector derivation apparatus of the present invention, the spectrum deriving section may be arranged to derive the spectrum based on eigenvectors of a noise subspace obtained from the measurement results from the sensors.

According to the signal vector derivation apparatus of the present invention, the sum of the first coefficients multiplied by the second coefficients may be a transfer function in the MUSIC method.

According to the signal vector derivation apparatus of the present invention, a number of the local maximum values may be two or more.

According to the present invention, the signal vector derivation apparatus may further include a position deriving section arranged to derive positions of the voxels in which the respective signal sources exist based on the spectrum.

According to the signal vector derivation apparatus of the present invention, the position deriving section may be arranged to derive the positions of the voxels in which the respective signal sources exist based on maximum values of each spectrum within the respective voxels.

According to the signal vector derivation apparatus of the present invention, the position deriving section may be arranged to: obtain weighted center of the voxels having the maximum values within a predetermined range from maximum of the maximum values, while increasing the predetermined range, until a number of times of the weighted center changing over a predetermined amount added by 1 reaches a number of the signal sources, cluster the voxels for which the weighted center is obtained into the number of the signal sources, and determine position of one of the clustered voxels with the maximum spectrum as the positions of the voxels in which the respective signal sources exist.

According to the signal vector derivation apparatus of the present invention, the positions of the voxels in which the respective signal sources exist may be further derived with reduction in a size of each voxel based on the positions of the voxels in which the respective signal sources exist that have already been derived by the position deriving section.

According to the present invention, a signal vector derivation method for receiving measurement results from a plurality of sensors that receive signals each represented by a vector having a predetermined direction and measure triaxial components orthogonal to each other and for deriving the direction of the vector, the measurement results from the sensors each proportional to a sum of the triaxial components of the vector multiplied, respectively, by first coefficients, includes: deriving a spectrum obtained based on the measurement results from the sensors and a sum of the first coefficients multiplied, respectively, by second coefficients, the spectrum having local maximum values within voxels in which signal sources that output the respective signals exist; and deriving the direction of the vector based on the second coefficients used to obtain the spectrum.

The present invention is a program of instructions for execution by a computer to perform a signal vector derivation process for receiving measurement results from a plurality of sensors that receive signals each represented by a vector having a predetermined direction and measure triaxial components orthogonal to each other and for deriving the direction of the vector, the measurement results from the sensors each proportional to a sum of the triaxial components of the vector multiplied, respectively, by first coefficients, the signal vector derivation process, including: deriving a spectrum obtained based on the measurement results from the sensors and a sum of the first coefficients multiplied, respectively, by second coefficients, the spectrum having local maximum values within voxels in which signal sources that output the respective signals exist; and deriving the direction of the vector based on the second coefficients used to obtain the spectrum.

The present invention is a non-transitory computer-readable medium including a program of instructions for execution by a computer to perform a signal vector derivation process for receiving measurement results from a plurality of sensors that receive signals each represented by a vector having a predetermined direction and measure triaxial components orthogonal to each other and for deriving the direction of the vector, the measurement results from the sensors each proportional to a sum of the triaxial components of the vector multiplied, respectively, by first coefficients, the signal vector derivation process, including: deriving a spectrum obtained based on the measurement results from the sensors and a sum of the first coefficients multiplied, respectively, by second coefficients, the spectrum having local maximum values within voxels in which signal sources that output the respective signals exist; and deriving the direction of the vector based on the second coefficients used to obtain the spectrum.

MODES FOR CARRYING OUT THE INVENTION

A description will now be given of an embodiment of the present invention referring to drawings.

Figure 1:
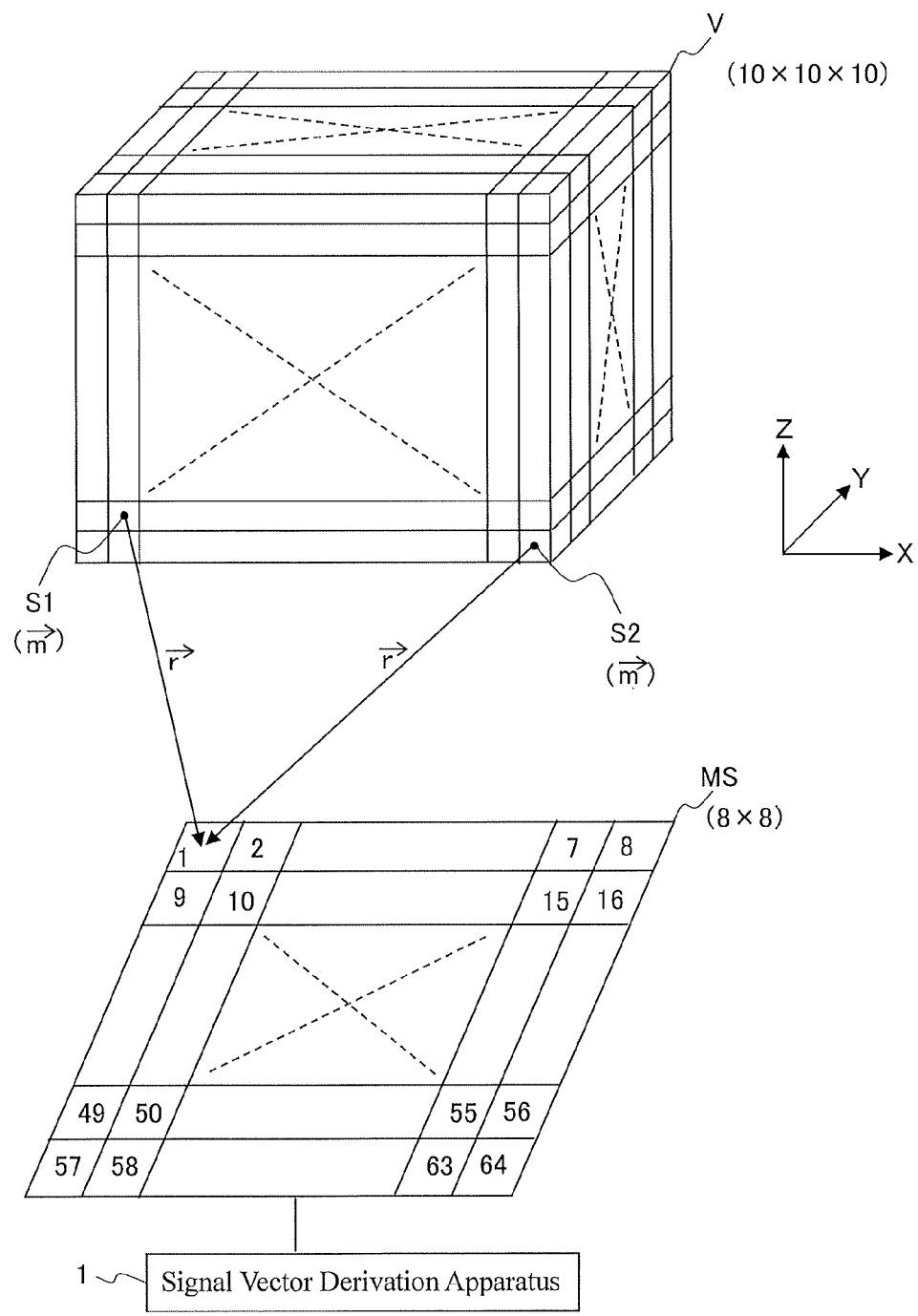
FIG. 1 is a perspective view showing voxels V and magnetic sensors MS according to an embodiment of the present invention.
Figure 2:
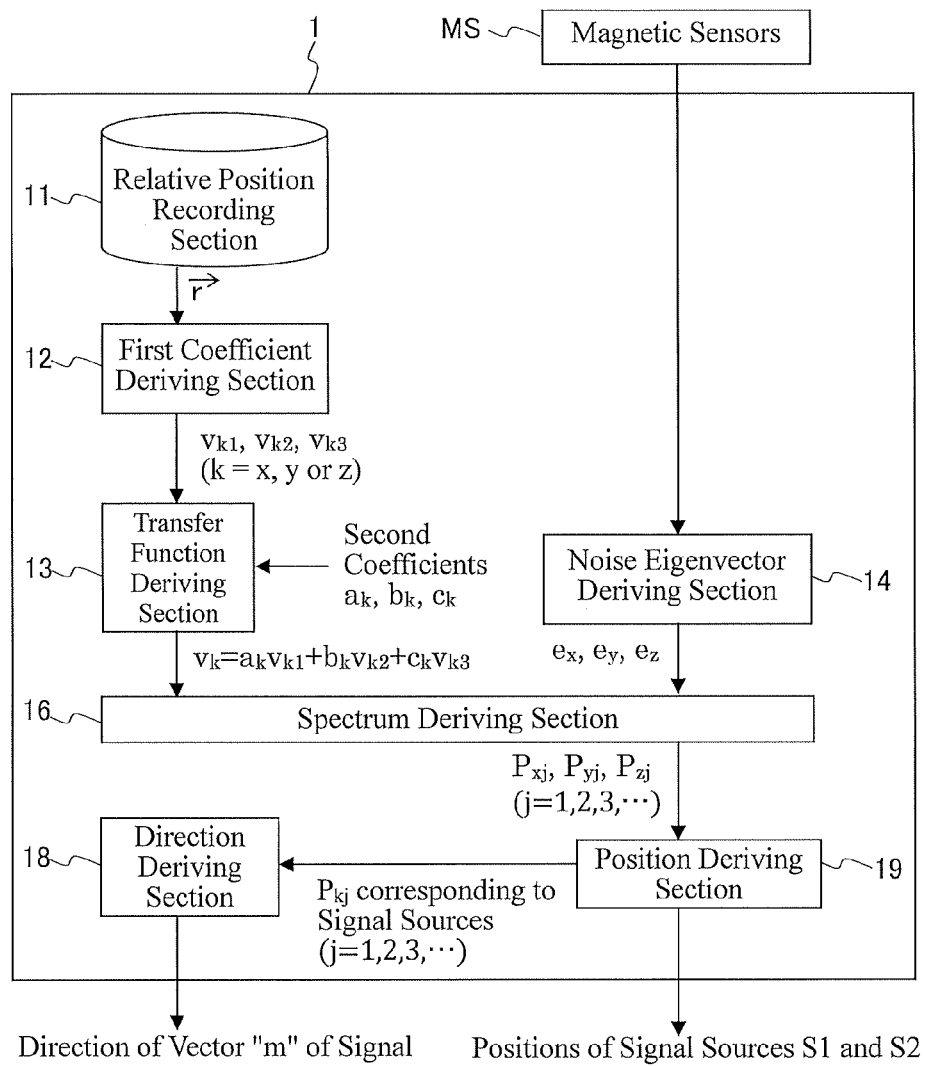
FIG. 2 is a functional block diagram showing the configuration of a signal vector derivation apparatus 1 according to the embodiment of the present invention.

FIG. 1 is a perspective view showing voxels V and magnetic sensors MS according to an embodiment of the present invention. FIG. 2 is a functional block diagram showing the configuration of a signal vector derivation apparatus 1 according to the embodiment of the present invention.

Referring to FIG. 1, signal sources S1 and S2 output signals. The signals are each represented by a vector "m" having a predetermined direction. The vector "m" is, for example, a magnetic dipole moment. It is noted that the number of signal sources is, for example, two, but may be three or more as long as it is less than the number of magnetic sensors MS. Note here that signals output from the signal sources have their respective frequencies or phases different from each other.

The positions within a space at which the signal sources S1 and S2 exist are also represented by voxels V (e.g. 10×10×10=1000 voxels). The signal sources S1 and S2 are positioned within their respective different voxels V. It is noted that the 1000 voxels V are denoted as V1 to V1000.

Multiple (e.g., 64 in 8 rows and 8 columns) magnetic sensors MS are arranged to receive signals (e.g., magnetic dipole moments) and measure X, Y, and Z triaxial components $B_x$, $B_y$, and $B_z$ orthogonal to each other. It is noted that the 64 magnetic sensors MS are denoted as MS1 to MS64.

Here given a directional vector "r" from a signal source (magnetic dipole) to a magnetic sensor MS, the magnetic flux density B (function of the vector "r") measured by the magnetic sensor MS is expressed by Biot-Savart's law as in formula (1), where $\mu_0$ is the magnetic constant. The vector "r" can also represent the positional relationship between each of the voxels V (V1 to V1000) and each of the magnetic sensors MS (MS1 to MS64).

$$B(\vec{r}) = \frac{\mu_0}{4\pi}\left\{\frac{3(\vec{m}\cdot\vec{r})}{|\vec{r}|^5}\vec{r} - \frac{\vec{m}}{|\vec{r}|^3}\right\} \tag{1}$$

From formula (1), $B_x$ is expressed as in formula (2) below, where $r_x$, $r_y$, and $r_z$ are x-, y-, and z-components of the vector "r", respectively and $m_x$, $m_y$, and $m_z$ are x-, y-, and z-components of the vector "m", respectively.

$$B_x = \frac{\mu_0}{4\pi}\left\{\left(\frac{3r_x^2}{|\vec{r}|^5} - \frac{1}{|\vec{r}|^3}\right)m_x + \frac{3r_xr_y}{|\vec{r}|^5}m_y + \frac{3r_zr_x}{|\vec{r}|^5}m_z\right\} \tag{2}$$

$$B_x = \frac{\mu_0}{4\pi}(v_{x1}m_x + v_{x2}m_y + v_{x3}m_z) \tag{2'}$$

Here, when the coefficients of $m_x$, $m_y$, and $m_z$ in formula (2) are replaced, respectively, with $v_{x1}$, $v_{x2}$, and $v_{x3}$, the formula (2) is expressed as in formula (2'). The measurement result $B_x$ from each magnetic sensor MS is then proportional to the sum $(v_{x1}m_x+v_{x2}m_y+v_{x3}m_z)$ of the X, Y, and Z triaxial components $m_x$, $m_y$, and $m_z$ of the vector "m" multiplied, respectively, by $v_{x1}$, $v_{x2}$, and $v_{x3}$ (first coefficients).

From formula (1), $B_y$ is expressed as in formula (3) below.

$$B_y = \frac{\mu_0}{4\pi}\left\{\frac{3r_xr_y}{|\vec{r}|^5}m_x + \left(\frac{3r_y^2}{|\vec{r}|^5} - \frac{1}{|\vec{r}|^3}\right)m_y + \frac{3r_yr_z}{|\vec{r}|^5}m_z\right\} \quad (3)$$

$$B_y = \frac{\mu_0}{4\pi}(v_{y1}m_x + v_{y2}m_y + v_{y3}m_z) \quad (3')$$

Here, when the coefficients of $m_x$, $m_y$, and $m_z$ in formula (3) are replaced, respectively, with $v_{y1}$, $v_{y2}$, and $v_{y3}$, the formula (3) is expressed as in formula (3'). The measurement result $B_y$ from each magnetic sensor MS is then proportional to the sum $(v_{y1}m_x+v_{y2}m_y+v_{y3}m_z)$ of the X, Y, and Z triaxial components $m_x$, $m_y$, and $m_z$ of the vector "m" multiplied, respectively, by $v_{y1}$, $v_{y2}$, and $v_{y3}$ (first coefficients).

From formula (1), $B_z$ is expressed as in formula (4) below.

$$B_z = \frac{\mu_0}{4\pi}\left\{\frac{3r_zr_x}{|\vec{r}|^5}m_x + \frac{3r_yr_z}{|\vec{r}|^5}m_y + \left(\frac{3r_z^2}{|\vec{r}|^5} - \frac{1}{|\vec{r}|^3}\right)m_z\right\} \quad (4)$$

$$B_z = \frac{\mu_0}{4\pi}(v_{z1}m_x + v_{z2}m_y + v_{z3}m_z) \quad (4')$$

Here, when the coefficients of $m_x$, $m_y$, and $m_z$ in formula (4) are replaced, respectively, with $v_{z1}$, $v_{z2}$, and $v_{z3}$, the formula (4) is expressed as in formula (4'). The measurement result $B_z$ from each magnetic sensor MS is then proportional to the sum $(v_{z1}m_x+v_{z2}m_y+v_{z3}m_z)$ of the X, Y, and Z triaxial components $m_x$, $m_y$, and $m_z$ of the vector "m" multiplied, respectively, by $v_{z1}$, $v_{z2}$, and $v_{z3}$ (first coefficients).

It is noted that referring to formulae (2) to (4) and (2') to (4'), $v_{x1}$, $v_{x2}$, $v_{x3}$, $v_{y1}$, $v_{y2}$, $v_{y3}$, $v_{z1}$, $v_{z2}$, and $v_{z3}$ (first coefficients) are defined based on the vector "r".

Referring to FIG. 2, the signal vector derivation apparatus 1 according to the embodiment of the present invention includes a relative position recording section 11, a first coefficient deriving section 12, a transfer function deriving section 13, a noise eigenvector deriving section 14, a spectrum deriving section 16, a direction deriving section 18, and a position deriving section 19.

The signal vector derivation apparatus 1 is arranged to receive measurement results from the multiple sensors MS1 to MS64 and derive the direction of the vector "m".

The relative position recording section 11 is arranged to record a vector "r" as a relative position between each of the 1000 voxels V and each of the magnetic sensors MS (MS1 to MS64).

The first coefficient deriving section 12 is arranged to read the vector "r" out of the relative position recording section 11 and derive first coefficients $v_{x1}$, $v_{x2}$, $v_{x3}$, $v_{y1}$, $v_{y2}$, $v_{y3}$, $v_{z1}$, $v_{z2}$, and $v_{z3}$ (see formulae (2) to (4) and (2') to (4')).

For example, the first coefficient $v_{x1}$ is expressed as in formula (5) below.

$$v_{x1} = \begin{pmatrix} v_{x1}(1,1) & \cdots & v_{x1}(1,1000) \\ \vdots & \ddots & \vdots \\ v_{x1}(64,1) & \cdots & v_{x1}(64,1000) \end{pmatrix} \quad (5)$$

The vector "r" is determined by the position of each voxel V and the position of each magnetic sensor MS and thereby has 1000×64 different candidate values. Accordingly, the first coefficient $v_{x1}$ also has 1000×64 different candidate values. In formula (5), the 1st row denotes $v_{x1}$ for the magnetic sensor MS1, the 2nd row denotes $v_{x1}$ for the magnetic sensor MS2, . . . , and the 64th row denotes $v_{x1}$ for the magnetic sensor MS64. Further, in formula (5), the 1st column denotes $v_{x1}$ for the voxel V1, the 2nd column denotes $v_{x1}$ for the voxel V2, . . . , and the 1000th column denotes $v_{x1}$ for the voxel V1000. For example, the element $v_{x1}$ (1, 1000) of the 1 st row and the 1000th column in formula (5) denotes $v_{x1}$ for the magnetic sensor MS1 and the voxel V1000. That is, $v_{x1}$ (1, 1000) can be obtained by substituting the vector "r" as a directional vector from the voxel V1000 to the magnetic sensor MS1 into the coefficient of $m_x$ in formula (2).

The other first coefficients $v_{x2}$, $v_{x3}$, $v_{y1}$, $v_{y2}$, $v_{y3}$, $v_{z1}$, $v_{z2}$, and $v_{z3}$ also each have 1000×64 different candidate values.

The first coefficient $v_{x1}$ is normalized as in formula (6) below for subsequent processing, though may be used without normalization.

$$v_{x1}(h,n)/(v_{x1}(1,n)^2 + v_{x1}(2,n)^2 + \ldots + v_{x1}(64,n)^2)^{1/2} \quad (6)$$

Here, "h" and "n" represent row and column, respectively. That is, the first coefficient $v_{x1}$ of the h-th row and the n-th column is divided by the square root of the sum of the squares of the first coefficients $v_{x1}$ of the 1st, 2nd, . . . , 64th rows and the n-th column to be a new first coefficient $v_{x1}$ of the h-th row and the n-th column.

The other first coefficients $v_{x2}$, $v_{x3}$, $v_{y1}$, $v_{y2}$, $v_{y3}$, $v_{z1}$, $v_{z2}$, and $v_{z3}$ are also normalized.

The first coefficient deriving section 12 is arranged to output the thus normalized first coefficients.

The noise eigenvector deriving section 14 is arranged to obtain eigenvectors of a noise subspace from the measurement results $B_x$, $B_y$, and $B_z$ from each magnetic sensor MS according to the MUSIC method.

$X(t)_x$ is first obtained from the measurement result $B_x$ from each magnetic sensor MS as in formula (7) below, where, "t" is the time of measurement and T represents transposition.

$$X(t)_x = \begin{pmatrix} B_{x1}(t1) & B_{x2}(t1) & \cdots & B_{x64}(t1) \\ B_{x1}(t2) & B_{x2}(t2) & \cdots & B_{x64}(t2) \\ \cdots & & & \\ B_{x1}(tN) & B_{x2}(tN) & \cdots & B_{x64}(tN) \end{pmatrix}^T \quad (7)$$

$X(t)_x$ is a transposed matrix describing $B_x$ measured at time t1 in the 1st row, $B_x$ measured at time t2 in the 2nd row, . . . , $B_x$ measured at time tN in the Nth row and $B_x$ measured by the magnetic sensor M1 in the 1st column, $B_x$ measured by the magnetic sensor M2 in the 2nd column, . . . , $B_x$ measured by the magnetic sensor M64 in the 64th column.

$X(t)_x$ is used to obtain a correlation matrix as in formula (8) below.

$$E\{X(t)_x X(t)_x^T\} \quad (8)$$

Here, E represents the ensemble average. A matrix of 64 rows and 64 columns is obtained from formula (8). Eigenvalues and eigenvectors are then obtained of the correlation matrix obtained from formula (8). Among the thus obtained eigenvalues, the ones for the number of the signal sources (2) are large, while the remaining (64−2=62) eigenvalues are small. Eigenvectors ex of the noise subspace are then obtained correspondingly to the smaller eigenvalues. Each of the eigenvectors ex of the noise subspace is a vector of 64 rows and 1 column. 62 eigenvectors ex of the noise subspace exist correspondingly to the smaller eigenvalues.

It is noted that eigenvectors ey of the noise subspace can also be obtained similarly. First, $B_x$ in formula (7) is replaced with $B_y$ and $X(t)_x$ in formulae (7) and (8) is replaced with $X(t)_y$, and formula (8) is used to obtain a correlation matrix. Then, in a similar manner as above, eigenvectors ey of the noise subspace are obtained correspondingly to the smaller eigenvalues. Each of the eigenvectors ey of the noise subspace is a vector of 64 rows and 1 column. 62 eigenvectors ey of the noise subspace exist correspondingly to the smaller eigenvalues.

Eigenvectors ez of the noise subspace can also be obtained similarly. First, $B_x$ in formula (7) is replaced with $B_z$ and $X(t)_x$ in formulae (7) and (8) is replaced with $X(t)_z$, and formula (8) is used to obtain a correlation matrix. Then, in a similar manner as above, eigenvectors ez of the noise subspace are obtained correspondingly to the smaller eigenvalues. Each of the eigenvectors ez of the noise subspace is a vector of 64 rows and 1 column. 62 eigenvectors ez of the noise subspace exist correspondingly to the smaller eigenvalues.

The transfer function deriving section 13 is arranged to derive transfer functions $v_x$, $v_y$, and $v_z$ as in formulae (9), (10), and (11) below. The sum of the first coefficients $v_{x1}$, $v_{x2}$, and $v_{x3}$ multiplied, respectively, by the second coefficients $a_x$, $b_x$, and $c_x$ is derived (see formula (9)). The derivation result is the transfer function $v_x$. The sum of the first coefficients $v_{y1}$, $v_{y2}$, and $v_{y3}$ multiplied, respectively, by the second coefficients $a_y$, $b_y$, and $c_y$ is derived (see formula (10)). The derivation result is the transfer function $v_y$. The sum of the first coefficients $v_{z1}$, $v_{z2}$, and $v_{z3}$ multiplied, respectively, $b_y$ the second coefficients $a_z$, $b_z$, and $c_z$ is derived (see formula (11)). The derivation result is the transfer function $v_z$.

$$v_x = a_x v_{x1} + b_x v_{x2} + c_x v_{x3} \quad (9)$$

$$v_y = a_y v_{y1} + b_y v_{y2} + c_y v_{y3} \quad (10)$$

$$v_z = a_z v_{z1} + b_z v_{z2} + c_z v_{z3} \quad (11)$$

It is noted that the transfer functions $v_x$, $v_y$, and $v_z$ are the transfer functions in the MUSIC method.

Also, the second coefficients may each be a value other than zero. For example, $a_x = b_x = c_x = 1$ (i.e., $v_x = v_{x1} + v_{x2} + v_{x3}$) may be set, $a_y = b_y = 1$ and $c_y = -1$ (i.e., $v_y = v_{y1} + v_{y2} - v_{y3}$) may be set, or $a_z = 1$, $b_z = -1$, and $c_z = 1$ (i.e., $v_z = v_{z1} - v_{z2} + v_{z3}$) may be set.

Note here that any one or two of the second coefficients may be zero. For example, $a_x = 1$ and $b_x = c_x = 0$ (i.e., $v_x = v_{x1}$) may be set or $a_x = b_x = 1$ and $c_x = 0$ (i.e., $v_x = v_{x1} + v_{x2}$) may be set.

It is here assumed that $(a_k, b_k, c_k)$ (where k=x, y, z) can have the following 13 different candidate combinations: (1, 0, 0), (0, 1, 0), (0, 0, 1), (1, 1, 0), (1, -1, 0), (0, 1, 1), (0, 1, -1), (1, 0, 1), (-1, 0, 1), (1, 1, 1), (-1, 1, 1), (1, -1, 1), and (1, 1, -1). $v_k$ consists of $v_{k1}$, $v_{k2}$, ..., and $v_{k13}$, accordingly.

For example, if $(a_x, b_x, c_x) = (1, 0, 0)$, then $v_x = v_{x1}$. If $(a_x, b_x, c_x) = (1, 1, 0)$, then $v_x = v_{x4} = v_{x1} + v_{x2}$. If $(a_x, b_x, c_x) = (1, 1, -1)$, then $v_x = v_{x13} = v_{x1} + v_{x2} - v_{x3}$.

For example, if $(a_y, b_y, c_y) = (1, 0, 0)$, then $v_y = v_{y1}$. If $(a_y, b_y, c_y) = (1, 1, 0)$, then $v_y = v_{y4} = v_{y1} + v_{y2}$. If $(a_y, b_y, c_y) = (1, 1, -1)$, then $v_y = v_{y13} = v_{y1} + v_{y2} - v_{y3}$.

For example, if $(a_z, b_z, c_z) = (1, 0, 0)$, then $v_z = v_{z1}$. If $(a_z, b_z, c_z) = (1, 1, 0)$, then $v_z = v_{z4} = v_{z1} + v_{z2}$. If $(a_z, b_z, c_z) = (1, 1, -1)$, then $v_z = v_{z13} = v_{z1} + v_{z2} - v_{z3}$.

The spectrum deriving section 16 is arranged to derive a spectrum having local maximum values within the voxels V in which the signal sources S1 and S2 exist. Such a spectrum is obtained according to the MUSIC method. The spectrum has two local maximum values correspondingly to the number of signal sources. It is noted that if the number of signal sources is three or more, the spectrum also has three or more local maximum values accordingly.

Spectrums are derived by the spectrum deriving section 16 based on (the eigenvectors ex, ey, and ez of the noise subspace obtained from) the measurement results $B_x$, $B_y$, and $B_z$ from each magnetic sensor MS and the sum of the first coefficients multiplied, respectively, $b_y$ the second coefficients (i.e. transfer functions $v_x$, $v_y$, and $v_z$) (formulae (9), (10), (11)). The spectrum deriving section 16 is arranged to derive spectrums based on the transfer functions $v_x$, $v_y$, and $v_z$ output from the transfer function deriving section 13 and the eigenvectors ex, ey, and ez of the noise subspace output from the noise eigenvector deriving section 14.

The spectrum deriving section 16 is arranged to derive the spectrum $P_{x1}$ as follows.

(1) There are 62 eigenvectors ex (of 64 rows and 1 column) in the noise subspace, and these vectors ex are arranged in 62 columns to be a matrix of 64 rows and 62 columns.

(2) the matrix ex is transposed and $b_y$ which the transfer function $v_{x1}$ (a matrix of 64 rows and 1000 columns) is multiplied. That is, $ex^T v_{x1}$ is obtained. This is a matrix of 62 rows and 1000 columns.

(3) Each element of the matrix obtained in (2) is squared.

(4) The elements of the matrix obtained in (3) are summed for each column and arranged in a row to obtain a matrix of 1 row and 1000 columns. For example, (1, Q) element+(2, Q) element+ ... +(62, Q) element of the matrix obtained in (3) results in the (1, Q) element of the matrix of 1 row and 1000 columns obtained in (4) (where Q is an integer of 1 to 1000).

(5) Each element of the matrix obtained in (4) is inverted to obtain a spectrum $P_{x1}$ (a matrix of 1 row and 1000 columns).

It is noted that the columns of the spectrum $P_{x1}$ corresponds, respectively, to the voxels V1 to V1000. The same applies to the other spectrums.

The spectrum deriving section 16 is also arranged to derive the spectrums $P_{x2}$, $P_{x3}$, ..., and $P_{x13}$. The spectrums $P_{x2}$, $P_{x3}$, ..., and $P_{x13}$ can be derived by replacing the transfer function $v_{x1}$ in (2) above, respectively, with $v_{x2}$, $v_{x3}$, ..., and $v_{x13}$.

The spectrum deriving section 16 is arranged to derive the spectrums $P_{y1}$, $P_{y2}$, $P_{y3}$, ..., and $P_{y13}$. The spectrums $P_{y1}$, $P_{y2}$, $P_{y3}$, ..., and $P_{y13}$ can be derived by replacing the eigenvector ex of the noise subspace in (1) above with ey and replacing the transfer function $v_{x1}$ in (2) above, respectively, with $v_{y1}$, $v_{y2}$, $v_{y3}$, ..., and $v_{y13}$.

The spectrum deriving section 16 is arranged to derive the spectrums $P_{z1}$, $P_{z2}$, $P_{z3}$, ..., and $P_{z13}$. The spectrums $P_{z1}$, $P_{z2}$, $P_{z3}$, ..., and $P_{z13}$ can be derived by replacing the eigenvector ex of the noise subspace in (1) above with ez and replacing the transfer function $v_{x1}$ in (2) above, respectively, with $v_{z1}$, $v_{z2}$, $v_{z3}$, ..., and $v_{z13}$.

The position deriving section 19 is arranged to derive the positions of the voxels V in which the signal sources S1 and S2 exist based on the spectrums $P_{x1}$, $P_{x2}$, $P_{x3}$, ..., $P_{x13}$, $P_{y1}$, $P_{y2}$, $P_{y3}$, ..., $P_{y13}$, $P_{z1}$, $P_{z2}$, $P_{z3}$, ..., $P_{z13}$.

The spectrums output from the spectrum deriving section 16 are expressed as in formula (12) below.

$$P\text{ Matrix} = \begin{pmatrix} P_{x1} \\ \vdots \\ P_{x13} \\ P_{y1} \\ \vdots \\ P_{y13} \\ P_{z1} \\ \vdots \\ P_{z13} \end{pmatrix} \quad (12)$$

The maximum values P of each spectrum within the respective voxels (i.e. the maximum values in each column of formula (12)) are obtained (see formula (13)).

$$P = \max(P\text{Matrix}) \quad (13)$$

Since the number of columns (corresponding to voxels) having local maximum values in P corresponds to the number of signal sources (2), the signal sources S1 and S2 exist within the voxels corresponding to the columns. A method of detecting columns with local maximum values will hereinafter be described.

Figure 3:
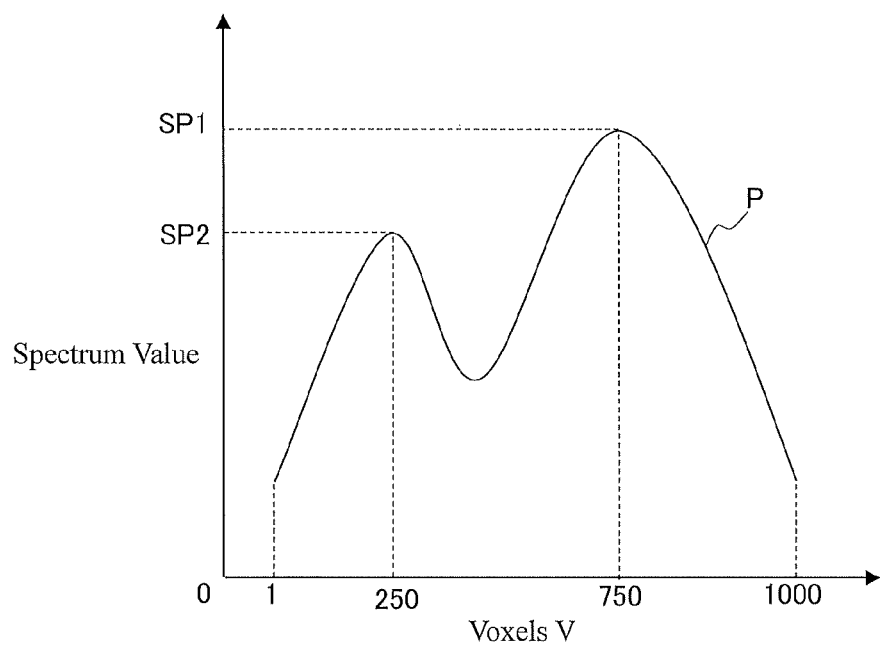
FIG. 3 is an example graph of the maximum values P.

FIG. 3 is an example graph of the maximum values P. In FIG. 3, the vertical axis represents the spectrum value, while the horizontal axis represents the voxels (V1 to V1000).

Referring to FIG. 3, it is provided that (the spectrum with) the maximum value P has a value of SP1 (local maximum value) within the voxel V750 and (the spectrum with) the maximum value P has a value of SP2 (local maximum value) within the voxel V250. Note here that SP1 is larger than SP2.

The position deriving section 19 is arranged to obtain the weighted center of the voxels having the maximum values P within a predetermined range from the maximum SP1 of the maximum values P (e.g. the maximum values P of 0.95SP1 or more), while increasing the predetermined range (e.g. the predetermined range is extended by 0.05SP1, such as the maximum values P of 0.95SP1 or more→0.90SP1 or more→0.85SP1 or more→ . . . ), until the number of times of the weighted center changing over a predetermined amount added by 1 reaches the number of the signal sources (2).

The weighted center of the voxels in the vicinity of the maximum SP1 of the maximum values P is around the voxel V750. However, when the predetermined range extends from the maximum SP1 to include SP2, the weighted center of the voxels shifts lower from voxel V750. The weighted center then changes over a predetermined amount and the number of times (1) added by 1 reaches the number of the signal sources (2), where obtaining the weighted center of the voxels is completed.

Next, the voxels for which the weighted center is thus obtained is clustered into the number of the signal sources (2). For example, Kmeans clustering, which is unsupervised machine learning, is performed for labeling by the number of the signal sources.

Finally, the positions of the ones of the clustered voxels with the maximum spectrum are determined as the positions of the voxels in which the respective signal sources exist.

It is noted that the position deriving section 19 may further reduce the size of each voxel, based on the positions of the voxels in which the thus derived signal sources exist, to derive the positions of the voxels in which the respective signal sources exist. It is thus possible to calculate the positions of the voxels in which the signal sources exist with high accuracy and speed.

The direction deriving section 18 is arranged to receive $P_{kj}$ (where k=x, y, z and j=1, 2, 3, . . . ) corresponding to the signal sources S1 and S2 (i.e. having local maximum values in P) from the position deriving section 19. The direction deriving section 18 is further arranged to derive the direction of the vector "m" based on the second coefficients used to obtain $P_{kj}$ corresponding to the signal sources S1 and S2.

For example, it is assumed that $P_{x13}$ ($P_{y13}$ or $P_{z13}$) of the 750th column (voxel V750) and $P_{x4}$ ($P_{y4}$ or $P_{z4}$) of the 250th column (voxel V250) are provided as spectrums corresponding to the respective signal sources S1 and S2 from the position deriving section 19 to the direction deriving section 18.

The direction deriving section 18 then derives that the second coefficient ($a_k$, $b_k$, $c_k$) (where k=x, y, z) to be (1, 1, −1), which is used to obtain $P_{x13}$ ($P_{y13}$ or $P_{z13}$) as the direction of the vector "m" at the signal source S1 within the voxel V750. Accordingly, the direction deriving section 18 derives the direction of the vector "m" at the signal source S1 within the voxel V750 to be parallel to the vector (1, 1, −1). Note here that the vector (1, 1, −1) is a vector having an X component of 1, a Y component of 1, and a Z component of −1.

The direction deriving section 18 further derives that the second coefficient ($a_k$, $b_k$, $c_k$) (where k=x, y, z) to be (1, 1, 0), which is used to obtain $P_{x4}$ ($P_{y4}$ or $P_{z4}$) as the direction of the vector "m" at the signal source S2 within the voxel V250. Accordingly, the direction deriving section 18 derives the direction of the vector "m" at the signal source S2 within the voxel V250 to be parallel to the vector (1, 1, 0). Note here that the vector (1, 1, 0) is a vector having an X component of 1, a Y component of 1, and a Z component of 0.

Next will be described an operation according to the embodiment of the present invention.

The first coefficient deriving section 12 reads the vector "r" out of the relative position recording section 11 and derives first coefficients $v_{x1}$, $v_{x2}$, $v_{x3}$, $v_{y1}$, $v_{y2}$, $v_{y3}$, $v_{z1}$, $v_{z2}$, and $v_{z3}$ (see formulae (2) to (4) and (2') to (4')).

It is noted that the first coefficients, which have 1000×64 different candidate values (see formula (5)), are normalized (see formula (6)) and provided to the transfer function deriving section 13.

The transfer function deriving section 13 derives transfer functions $v_x$, $v_y$, and $v_z$ based on the first coefficients and the second coefficients $a_x$, $b_x$, $c_x$, $a_y$, $b_y$, $c_y$, $a_z$, $b_z$, $c_z$ (see formulae (9), (10), and (11)).

The noise eigenvector deriving section 14 derives eigenvectors ex, ey, and ez of a noise subspace from the measurement results $B_x$, $B_y$, and $B_z$ from each magnetic sensor MS according to the MUSIC method.

The spectrum deriving section 16 derives spectrums $P_{x1}$, $P_{x2}$, $P_{x3}$, . . . , $P_{x13}$, $P_{y1}$, $P_{y2}$, $P_{y3}$, . . . , $P_{y13}$, $P_{z1}$, $P_{z2}$, $P_{z3}$, . . . , $P_{z13}$ based on the transfer functions $v_x$, $v_y$, and $v_z$ and the eigenvectors ex, ey, and ez of the noise subspace (see formula (12)).

The position deriving section 19 obtains the maximum values P of each spectrum within the respective voxels (i.e. the maximum values in each column of formula (12)) (see formula (13) and FIG. 3). The voxels 250, 750 in which the signal sources S1 and S2 exist are derived based on the maximum values P.

The direction deriving section 18 derives the direction of the vector "m" based on the second coefficients used to obtain $P_{kj}$ corresponding to the signal sources S1 and S2.

The embodiment of the present invention improves the accuracy of measurement of a signal such as a magnetic field.

For example, if the transfer function $v_k$ only consists of $v_{k1}$, $v_{k2}$, and $v_{k3}$, the direction of the vector "m" can be measured only if in parallel with the X, Y, or Z direction. The direction of the vector "m", if in parallel with directions other than above (e.g. vector (1, 1, 0) (i.e. vector having an X component of 1, a Y component of 1, and a Z component of 0)), cannot be measured.

However, in accordance with the embodiment of the present invention, since the transfer function $v_k$ consists of many types including $v_{k1}$, $v_{k2}$, $v_{k3}$, . . . , and $v_{k13}$, the direction of the vector "m" can be measured even if not in parallel with the X, Y, and Z directions.

It is noted that the signal vector is not limited to a magnetic dipole moment, though have been descried as a magnetic dipole moment in the embodiment of the present invention. The signal vector may be, for example, an electric dipole moment (vector "p").

The magnetic flux density B (function of the vector "r") measured by the magnetic sensor MS is expressed as in formula (14).

$$B(\vec{r}) = \frac{\mu_0}{4\pi} \frac{(\vec{p} \times \vec{r})}{|\vec{r}|^3} \tag{14}$$

From formula (14), $B_x$ is expressed as in formula (15) below, where $p_x$, $p_y$, and $p_z$ are x-, y-, and z-components of the vector "p", respectively.

$$B_x = \frac{\mu_0}{4\pi}\left(\frac{r_z}{|\vec{r}|^3} p_y - \frac{r_y}{|\vec{r}|^3} p_z\right) \tag{15}$$

$$B_x = \frac{\mu_0}{4\pi}(v_{x1} p_x + v_{x2} p_y + v_{x3} p_z) \tag{15'}$$

Here, when the coefficients of $p_x$, $p_y$, and $p_z$ in formula (15) are replaced, respectively, with $v_{x1}$, $v_{x2}$, and $v_{x3}$, the formula (15) is expressed as in formula (15'). The measurement result $B_x$ from each magnetic sensor MS is then proportional to the sum ($v_{x1} p_x + v_{x2} p_y + v_{x3} p_z$) of the X, Y, and Z triaxial components $p_x$, $p_y$, and $p_z$ of the vector "p" multiplied, respectively, by $v_{x1}$, $v_{x2}$, and $v_{x3}$ (first coefficients). Note here that the component ($p_x$) of the vector in the same direction (X direction) as that of the component of the measurement result $B_x$ is zero, and the first coefficient $v_{x1}$ multiplying it is 1.

From formula (14), $B_y$ is expressed as in formula (16) below.

$$B_y = \frac{\mu_0}{4\pi}\left(\frac{r_x}{|\vec{r}|^3} p_z - \frac{r_z}{|\vec{r}|^3} p_x\right) \tag{16}$$

$$B_y = \frac{\mu_0}{4\pi}(v_{y1} p_x + v_{y2} p_y + v_{y3} p_z) \tag{16'}$$

Here, when the coefficients of $p_x$, $p_y$, and $p_z$ in formula (16) are replaced, respectively, with $v_{y1}$, $v_{y2}$, and $v_{y3}$, the formula (16) is expressed as in formula (16'). The measurement result $B_y$ from each magnetic sensor MS is then proportional to the sum ($v_{y1} p_x + v_{y2} p_y + v_{y3} p_z$) of the X, Y, and Z triaxial components $p_x$, $p_y$, and $p_z$ of the vector "p" multiplied, respectively, by $v_{y1}$, $v_{y2}$, and $v_{y3}$ (first coefficients). Note here that the component ($p_y$) of the vector in the same direction (Y direction) as that of the component of the measurement result $B_y$ is zero, and the first coefficient $v_{y2}$ multiplying it is 1.

From formula (14), $B_z$ is expressed as in formula (17) below.

$$B_z = \frac{\mu_0}{4\pi}\left(\frac{r_y}{|\vec{r}|^3} p_x - \frac{r_x}{|\vec{r}|^3} p_y\right) \tag{17}$$

$$B_z = \frac{\mu_0}{4\pi}(v_{z1} p_x + v_{z2} p_y + v_{z3} p_z) \tag{17'}$$

Here, when the coefficients of $p_x$, $p_y$, and $p_z$ in formula (17) are replaced, respectively, with $v_{z1}$, $v_{z2}$, and $v_{z3}$, the formula (17) is expressed as in formula (17'). The measurement result $B_z$ from each magnetic sensor MS is then proportional to the sum ($v_{z1} p_x + v_{z2} p_y + v_{z3} p_z$) of the X, Y, and Z triaxial components $p_x$, $p_y$, and $p_z$ of the vector "p" multiplied, respectively, by $v_{z1}$, $v_{z2}$, and $v_{z3}$ (first coefficients). Note here that the component ($p_z$) of the vector in the same direction (Z direction) as that of the component of the measurement result $B_z$ is zero, and the first coefficient $v_{z3}$ multiplying it is 1.

The configuration and operation of the signal vector derivation apparatus 1 is the same as those when the signal vector is a magnetic dipole moment (vector "m") and will not be described.

The above-described embodiment may also be implemented as follows. A computer including a CPU, a hard disk, and a medium (USB memory, CD-ROM, or the like) reading device is caused to read a medium with a program recorded thereon that achieves the above-described components (e.g. the relative position recording section 11, the first coefficient deriving section 12, the transfer function deriving section 13, the noise eigenvector deriving section 14, the spectrum deriving section 16, the direction deriving section 18, and the position deriving section 19) and install the program in the hard disk. The above-described features can also be achieved in this manner.

DESCRIPTION OF REFERENCE NUMERAL

1 Signal Vector Derivation Apparatus
11 Relative Position Recording Section
12 First Coefficient Deriving Section
13 Transfer Function Deriving Section
14 Noise Eigenvector Deriving Section
16 Spectrum Deriving Section
18 Direction Deriving Section
19 Position Deriving Section
MS Magnetic Sensor
V Voxel
B Magnetic Flux Density
$v_{x1}$, $v_{x2}$, $v_{x3}$, $v_{y1}$, $v_{y2}$, $v_{y3}$, $v_{z1}$, $v_{z2}$, $v_{z3}$ First Coefficients
$a_k$, $b_k$, $c_k$ Second Coefficients
$v_{k1}$, $v_{k2}$, . . . , $v_{k13}$ Transfer Function
S1, S2 Signal Source
m Vector (Magnetic Dipole Moment)
ex, ey, ez Eigenvectors of the Noise Subspace
P Maximum Value

The invention claimed is:

1. A signal vector derivation apparatus for receiving measurement results from a plurality of sensors that receive signals each represented by a vector having a predetermined direction and measure triaxial components orthogonal to each other and for deriving the direction of the vector, the measurement results from the sensors each proportional to a sum of the triaxial components of the vector multiplied, respectively, by first coefficients, the signal vector derivation apparatus, comprising:

a spectrum deriving section arranged to derive a spectrum obtained based on the measurement results from the sensors and a sum of the first coefficients multiplied, respectively, by second coefficients, the spectrum having local maximum values within voxels in which signal sources that output the respective signals exist; and a direction deriving section arranged to derive the direction of the vector based on the second coefficients used to obtain the spectrum.

2. The signal vector derivation apparatus according to claim 1, wherein
the vector is a magnetic dipole moment or an electric dipole moment.

3. The signal vector derivation apparatus according to claim 1, wherein
the vector is an electric dipole moment, and
the component of the vector in the same direction as that of the component of each measurement result is zero.

4. The signal vector derivation apparatus according to claim 1, wherein
the first coefficients are defined based on the positional relationships between the respective voxels and the respective sensors.

5. The signal vector derivation apparatus according to claim 1, wherein
any one or two of the second coefficients are zero.

6. The signal vector derivation apparatus according to claim 1, wherein
the spectrum is obtained according to the MUSIC method.

7. The signal vector derivation apparatus according to claim 6, wherein
the spectrum deriving section is arranged to derive the spectrum based on eigenvectors of a noise subspace obtained from the measurement results from the sensors.

8. The signal vector derivation apparatus according to claim 6, wherein
the sum of the first coefficients multiplied by the second coefficients is a transfer function in the MUSIC method.

9. The signal vector derivation apparatus according to claim 1, wherein
a number of the local maximum values is two or more.

10. The signal vector derivation apparatus according to claim 1, further comprising a position deriving section arranged to derive positions of the voxels in which the respective signal sources exist based on the spectrum.

11. The signal vector derivation apparatus according to claim 10, wherein
the position deriving section is arranged to derive the positions of the voxels in which the respective signal sources exist based on maximum values of each spectrum within the respective voxels.

12. The signal vector derivation apparatus according to claim 11, wherein
the position deriving section is arranged to:
obtain weighted center of the voxels having the maximum values within a predetermined range from maximum of the maximum values, while increasing the predetermined range, until a number of times of the weighted center changing over a predetermined amount added by 1 reaches a number of the signal sources,
cluster the voxels for which the weighted center is obtained into the number of the signal sources, and
determine position of one of the clustered voxels with the maximum spectrum as the positions of the voxels in which the respective signal sources exist.

13. The signal vector derivation apparatus according to claim 10, wherein
the positions of the voxels in which the respective signal sources exist are further derived with reduction in a size of each voxel based on the positions of the voxels in which the respective signal sources exist that have already been derived by the position deriving section.

14. A signal vector derivation method for receiving measurement results from a plurality of sensors that receive signals each represented by a vector having a predetermined direction and measure triaxial components orthogonal to each other and for deriving the direction of the vector, the measurement results from the sensors each proportional to a sum of the triaxial components of the vector multiplied, respectively, by first coefficients, the signal vector derivation method, comprising:

deriving a spectrum obtained based on the measurement results from the sensors and a sum of the first coefficients multiplied, respectively, by second coefficients, the spectrum having local maximum values within voxels in which signal sources that output the respective signals exist; and deriving the direction of the vector based on the second coefficients used to obtain the spectrum.

15. A non-transitory computer-readable medium including a program of instructions for execution by a computer to perform a signal vector derivation process for receiving measurement results from a plurality of sensors that receive signals each represented by a vector having a predetermined direction and measure triaxial components orthogonal to each other and for deriving the direction of the vector, the measurement results from the sensors each proportional to a sum of the triaxial components of the vector multiplied, respectively, by first coefficients, the signal vector derivation process, comprising:

deriving a spectrum obtained based on the measurement results from the sensors and a sum of the first coefficients multiplied, respectively, by second coefficients, the spectrum having local maximum values within voxels in which signal sources that output the respective signals exist; and deriving the direction of the vector based on the second coefficients used to obtain the spectrum.

* * * * *